United States Patent [19]

Waddell et al.

[11] Patent Number: 4,522,199

[45] Date of Patent: Jun. 11, 1985

[54] BODY WEIGHT SUPPORT SYSTEM

[75] Inventors: Thomas P. Waddell, 1306 Broadview West, Downingtown, Pa. 19335; Robin Renzetti, Coatesville, Pa.

[73] Assignee: Thomas P. Waddell, Downingtown, Pa.

[21] Appl. No.: 521,965

[22] Filed: Aug. 11, 1983

[51] Int. Cl.³ .............................................. A61F 3/00
[52] U.S. Cl. ................................................. 128/80 G
[58] Field of Search ................. 128/80 R, 80 C, 80 F, 128/87 R, 88, 80 G; 3/22, 25, 26, 27, 29

[56] References Cited

U.S. PATENT DOCUMENTS

| 3,266,059 | 8/1966 | Stelle | 3/12.3 |
| 3,799,159 | 3/1974 | Scott | 3/22 X |
| 4,408,600 | 10/1983 | Davis | 128/80 R |
| 4,450,832 | 5/1984 | Waddell | 128/80 G |

Primary Examiner—John D. Yasko

Attorney, Agent, or Firm—Caesar, Rivise, Bernstein & Cohen, Ltd.

[57] ABSTRACT

A body weight support system for releasable securement to at least one leg of a person includes an upper support member adapted to be positioned above the knee and including an upper end adapted to be located immediately adjacent the buttocks-thigh interface to form a seat. A second, lower member adapted to be located beneath the knee and having a lower end adjacent the foot. A flexure assembly is located in the region of the knee and interconnects the first and second support members. The flexure assembly enables the person wearing the system to freely bend the knee through an angular range up to a predetermined angle at which a resistance exists to further flexure. An energy dampening section permits damped flexure of the flexure assembly beyond the predetermined angle to thereby absorb energy imparted to the support system by the person wearing it.

45 Claims, 11 Drawing Figures

BODY WEIGHT SUPPORT SYSTEM

BACKGROUND OF THE INVENTION

This invention relates generally to support structures, and more particularly to systems for supporting the body weight of a person to facilitate various recreational and/or vocational activities.

Various types of braces attachable to a wearer's leg are disclosed in the prior art. In connection with snow skiing applications, U.S. Pat. No. 3,928,872 (Johnson) discloses a pair of devices, each of which is securable to a leg of the skier to provide flexural knee and leg support. In each device a spring is employed to interconnect an upper support sleeve positioned about the skier's leg above the knee to a lower support sleeve positioned below the knee, and the stated objectives of the devices are to reduce weight load on the knees, absorb shock and reduce the strain when the knee flexes. The use of resilient spring means, as employed in the devices disclosed in the Johnson patent, appears to inherently produce an oscillatory or bouncing effect on the skier's body as the angle of his or her knee flexure changes during a ski run owing to the uneven terrain of a typical ski slope. The more rigid the spring, the more pronounced the rebounding effect will be, which effect is quite undesirable for controlled skiing. Moreover, the frequency of spring movement in the Johnson devices will likely rarely match the frequency of flexure of the knee as caused by the traversal of a skier over the terrain. Thus, the Johnson devices may tend to take the skier out of synchronism with the terrain, thereby further contributing to the loss of the skier's balance and control.

To obviate the deficiencies of the devices disclosed in the Johnson patent a body weight support system employing non-resilient flexure means was invented by Thomas P. Waddell, one of the joint inventors of the subject matter of the instant application, and is described in detail in copending application Ser. No. 411,404, filed on Aug. 25, 1982, and hereinafter referred to as the "Waddell application". The subject matter of the Waddell application is incorporated herein by reference.

In the support system disclosed in the Waddell application a brace is provided for securement to the legs of a person. The brace basically comprises a frame-like construction including an upper leg support section, a lower leg support section and flexure means between them. Securement means, such as conventional straps having buckles at one end thereof, are employed to attach the upper leg support section and the lower leg support section about the leg of the user. The upper leg support section extends along the thigh of the user and terminates at its upper end immediately adjacent the buttocks-thigh interface to form a seat. The lower leg support section is a tubular member of a generally U-shape having a pair of upwardly extending leg portions and an arcuate bottom portion. The leg portions extend upwardly along the lower leg and terminate adjacent the knee. The curved bottom portion of the lower leg support section is located adjacent the skier's boot, and is adapted to be attached thereto.

In the brace disclosed in the Waddell application the preferred non-resilient flexure means includes a pair of spaced-apart flexure assemblies. Each assembly is located adjacent the knee of the wearer and includes a plurality of disk-like cylindrical segments mounted for pivotal movement relative to each other. The disk-like segments of both assemblies are joined together by a common tensioning cable extending through aligned central passages in the segments. One end of the tensioning cable is connected to an adjustment means adapted to control the degree of slack in the cable, and thereby adjust and set the degree of flexure provided by the flexure assemblies. The opposite end of the tensioning cable is retained against movement in a frame member forming part of the upper leg support section.

In the support system disclosed in the Waddell application substantial resistance to further flexural movement of the knee is encountered once the flexure assemblies have moved through an annular range up to a predetermined angle set by the adjustment of the common tensioning cable. The slight, or residual resiliency exhibited by the flexure assemblies at the maximum flexure angle (i.e., when the tensioning cable is taut) is on the order of approximately 10% and results from the slight "give" inherent in the tensioning cable.

Although the system of the Waddell application overcomes the various problems enountered with resilient flexure means of the type disclosed in the Johnson patent, it may exhibit certain inherent undesirable characteristics during some uses. Specifically, as a skier is moving over the uneven terrain of a typical ski slope, his or her knee flexure will constantly be changing, and may actually reach the maximum flexure angle at several different times during the run. In the event that the skier's knees do reach the maximum flexure angle, the body may be "jolted" due to the substantial resistance to further flexural movement created by the tensioning cable once the maximum flexure angle of the flexure assemblies has been reached. The small, e.g., approximately 10%, resiliency inherent in the cable of the Waddell system does not relieve this jolting effect to the desired optional degree.

From the above discussion it should be apparent that the spring-type system disclosed in the Johnson patent can result in the loss of balance and control during a ski run due to excessive resiliency. While the use of the non-resilient flexure assemblies disclosed in the Waddell application overcomes the problems associated with the Johnson device, such assemblies may nevertheless cause undesired jolting of the skier's body.

U.S. Pat. No. 4,144,881 (Chappell) discloses an orthopedic prosthetic device which can be incorporated into a knee support. The device includes a plurality of interlocking links, in the form of crescent-shaped disks, that can be adjusted to permit a desired degree of motion in the plane of articulation. This device does not provide an upper body weight support system, and also has virtually no resiliency or ability to move once the knee reaches the adjusted degree of rotation of the links.

OBJECT OF THE INVENTION

It is a general object of the instant invention to provide a body weight support system which overcomes the disadvantages of the prior art systems.

It is a further object of this invention to provide a body weight support system which assists in absorbing shock forces transmitted to the wearer's body.

It is a further object of this invention to provide controlled support of a wearer's body during recreational activities, such as skiing.

It is a further object of this invention to provide a teaching or training aid for skiers.

It is a further object of the instant invention to provide a body weight support system for use on a person's leg to allow unimpeded flexing of the knee up to a predetermined angle and to permit additional damped flexing of the knee beyond the predetermined angle to avoid excessive jolting of the wearer of the support system.

SUMMARY OF THE INVENTION

These and other objects of the instant invention are achieved by providing a body weight support system adapted to be secured to at least one of the wearer's legs. The system includes a damped flexure means joined to an upper support means adapted to be secured to the wearer's leg adjacent the thigh region, and to a second support means adapted to be secured to the wearer's leg adjacent the calf region. When so secured the flexure means is located adjacent the knee. The flexure means enables the user to freely bend the knee through an angular range up to a predetermined angle at which a resistance exists to further flexure. Energy dampening means are connected to the flexure means for permitting damped flexure of the flexure means beyond said predetermined angle to absorb shocks transmitted to the body of the wearer.

Other objects and many of the attendant advantages of this invention will be readily appreciated as the same becomes better understood by reference to the following detailed description when considered in connection with the accompanying drawing.

DETAILED DESCRIPTION OF THE PREFERRED EMBODIMENT

Figures 1, 2, 2A, 10:
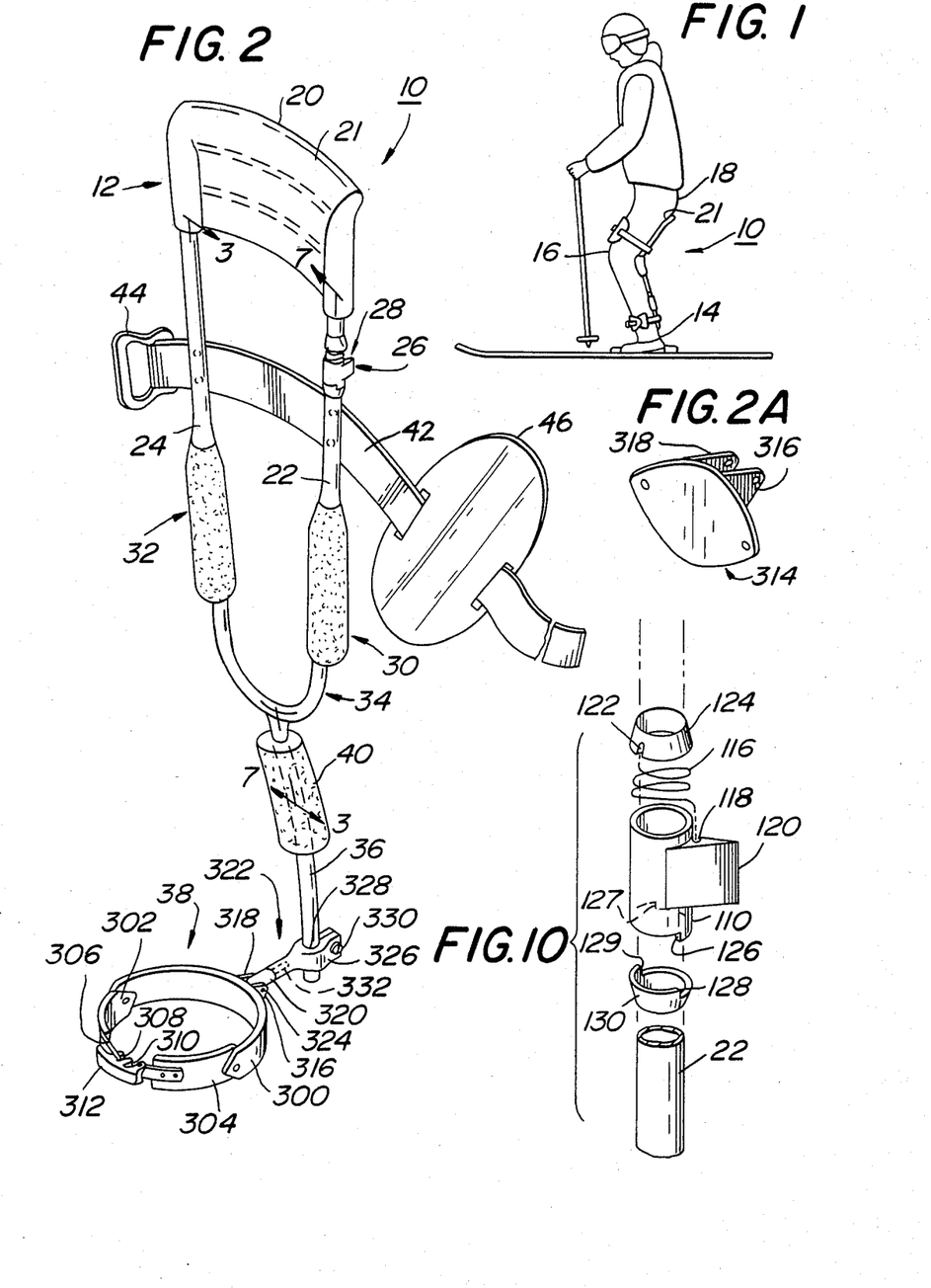
FIG. 1 is a side elevational view of a skier wearing a body weight support system of the instant invention.
FIG. 2 is an enlarged perspective view of the system shown in FIG. 1.
FIG. 2A is an enlarged isometric view of the connecting plate between the boot strap and the remainder of the system.
FIG. 10 is an enlarged exploded isometric view showing parts of the quick-release mechanism for adjusting the preset angular position up to which the flexure assemblies of the system can bend freely.

Referring now to the various figures of the drawings wherein like reference characters refer to like parts, there is shown in FIG. 1 a snow skier wearing the body weight support system 10 in accordance with the instant invention. A typical system 10 basically consists of a pair of braces 12 each of which is secured to a respective leg of the skier and to the ski boots 14 worn by the skier. While the system 10 shown herein consists of a pair of braces, this invention contemplates a body weight support system having only a single brace 12, such as would be used by a one legged skier. Even the single brace system is sufficient to provide all of the advantages of the invention for the skier. Moreover, while the remainder of the specification will be directed to the invention for use by skiers, and will describe the details of only one of the braces, it must be kept in mind that the system of this invention can be used for various applications where support of body weight is of importance.

As will be appreciated from the following specification, the system 10 shown herein is configured so that it can be readily adjusted to provide support for the skier so that the skier can readily assume and maintain the proper "attack" position, e.g., knees 16 bent forward of the boots 14 with the buttocks 18 centered over the boots. Additionally, a preferred embodiment of the invention permits the skier to sit or lean back with his or her buttocks rearwardly of the ski boots 14, but without supporting the body weight of the skier. Thus, the system of this invention is readily adapted to be used in teaching and training applications by encouraging the skier to maintain a proper posture relative to the boots and skis. If a proper posture is not maintained, the system of this invention will not support the skier.

Referring to FIG. 2 the brace 12 is in the form of a rigid frame formed by a pair of tubular frame sections 22 and 24, a generally U-shaped tubular bridging section 34 and a vertical support section 36. The upper sections 22 and 24 are connected to the top of the respective ends of the bridging section by flexure assemblies 30 and 32, respectively. When the brace is secured to the skier's leg the flexure assemblies are disposed adjacent the knee of the rear of the leg and towards each side of the leg. The brace also includes a top-fitting thigh support 20. Preferably this is an injection molded plastic member positioned over the upper ends of laterally spaced-apart upper support frame sections 22 and 24. The thigh support 20 has a generally concave inner curvature between the frame sections 22 and 24 to conform to the general shape of the thigh area. The uppermost end of the thigh support is generally rounded, and is flared back to provide a smooth surface 21 located adjacent the thigh-buttocks interface, to thereby form a seat. The upper frame sections 22 and 24 along with the thigh support 20 form the upper support means of the brace.

The upper frame section 22, being the outboard structure adjacent the lateral side (outside) of the skier's leg, includes a quick-adjustment system generally indicated by the numeral 26. This adjustment system is arranged to enable the presetting of the angle of flexure of the knee before increased resistance to further flexure occurs and includes components supported internally of the frame section 22 and actuating mechanism 28 located externally of said frame section, all of which will be described in detail hereinafter.

The upper support section 24, being the inboard structure located adjacent the medial side (inside) of the leg, houses a set of springs stacked in a column and a hydraulic dampening system to be described in detail hereinafter.

Referring again to FIG. 2 the flexure means of this invention includes laterally spaced-apart flexure assemblies 30 and 32 located between the upper support sections 22, 24, and the lower bridging section 34. The vertical support rod 36 has a slight concave curvature to conform to the leg of the wearer and extends downwardly from the bridging section 34 and is connected at its lower end to a ski boot attaching member 38. A cushioning pad 40 is secured about the vertical support section 36 to provide protection for a skier's leg, and in particular the shin area in the event a skier crosses his legs. In other words, the cushioning pad 40 prevents the skier from banging his or her shin into the back of the vertical support rod, and thereby prevents bruising or other injury to the skier's leg. The U-shaped lower bridging section 34 along with the support rod 36 provide the lower support means of the brace.

As can be seen in FIGS. 1 and 2 the brace 12 includes a mounting strap 42 for securing the brace to the leg. The strap is riveted to the laterally spaced-apart frame sections 22 and 24. The strap includes a buckle 44 at one end thereof, and the opposite end is adapted to receive a plate member 46 thereon. Preferably the plate 46 is a somewhat flexible molded member adapted to generally fit the contour of the leg. The primary purpose of this member is to spread the strap load over a wide surface to thereby avoid an undesired concentration of forces on the wearer's leg.

As mentioned earlier the quick adjustment system 26 permits presetting of the angle through which the flexure assemblies 30, 32 can freely move before experiencing any resistance to additional angular movement. In order to fully understand the manner in which the adjustment system 26 operates a brief description of the flexure assemblies will be set forth at this time.

Figure 3:
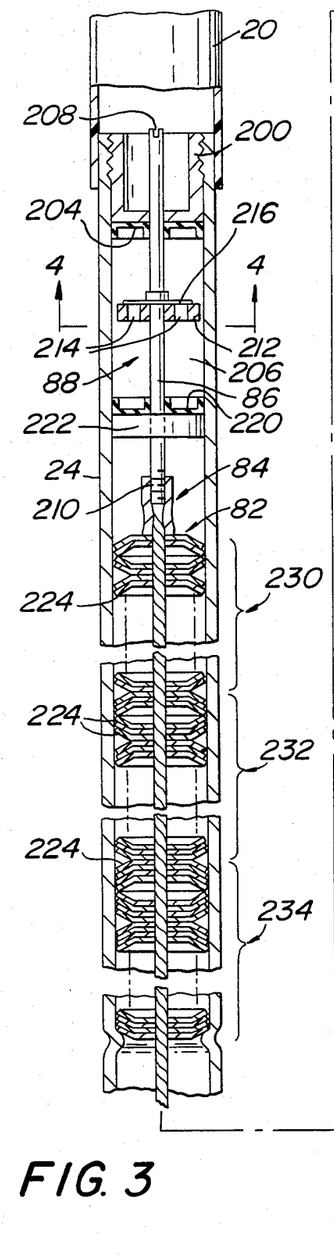
FIG. 3 is an enlarged fragmentary sectional view taken along line 3—3 of FIG. 2.
Figure 7:
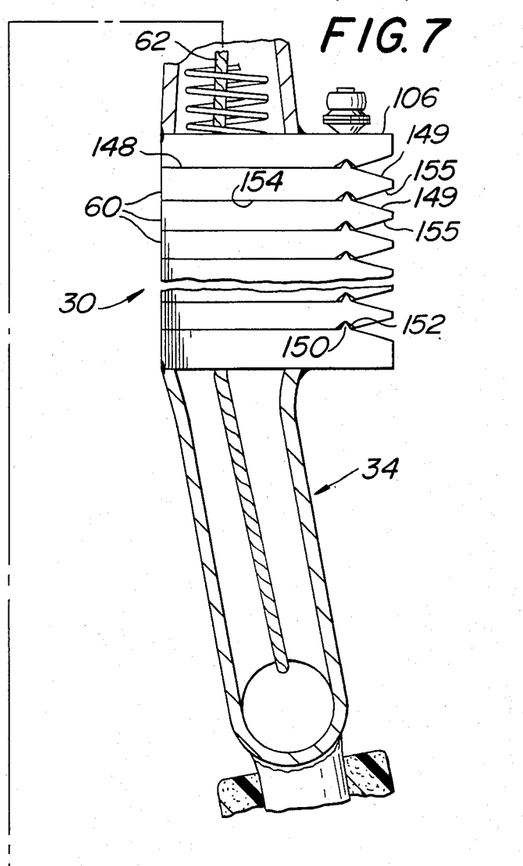
FIG. 7 is an enlarged fragmentary sectional view taken along line 7—7 of FIG. 2.

Referring specifically to FIGS. 3 and 7 each of the flexure assemblies 30, 32 includes a plurality of plate-like slugs 60 stacked upon each other, a power cable 62 extending through aligned passageways 64 adjacent the forward end of the stack (i.e., the end closest to the wearer's knee) and a taut alignment cable 66 extending through aligned passageways 68 adjacent the rear of the stack (i.e., the end furthest from the wearer's knee). The alignment cable 66 is maintained in a taut condition through the use of connectors 70 and 72 swaged to the opposed ends of said cable with disc springs 74 and 76 positioned between the connectors and the peripheral slugs in the stack.

It is the slack of the power cable 62 that is controlled by the adjustment system 26 to preset the angle through which the flexure assemblies 30 and 32 can freely pivot. That is, the amount of slack in the power cable 62 determines the angle through which the stack of slugs 60 can be bent before the cable becomes taut.

As can be seen best in FIG. 7 the power cable 62 extends continuously through an elongate sleeve 78 and compression spring 80 located within the upper frame section 22. Both this sleeve and spring form part of the adjustment system 26. The power cable 62 continues through the aligned passageways 64 (shown in FIG. 3) adjacent the forward end of the stack of slugs 60 of the flexure assembly 30. Thereafter the cable extends continuously through the hollow interior of the U-shaped lower bridging section 34, and then upwardly through the aligned passageways 64 at the forward end of the stack of slugs 60 of the flexure assembly 32 (FIG. 3). From this point the cable passes into the hollow upper support rod 24, and then through a dampening spring set 82 mounted therein. The upper end of the cable is attached through a swaged connection to the lower end of a connector 84. The upper end of the connector 84 is threaded to receive the threaded lower end of a piston rod 86 forming part of a hydraulic dampening system 88, to be described in detail hereinafter.

From the above description it should be apparent that the amount of slack established in the power cable 62 determines, or sets the angle through which the slugs 60 in each of the flexure assemblies 30 and 32 can be freely moved without encountering substantial resistance. Once the preset angular movement of the assemblies has taken place the power cable 62 becomes taut, and further angular movement is resisted by the dampening spring set 82 in a manner to be described in detail hereinafter.

Referring specifically to FIG. 7 the adjustment system 26 will now be described. As can be seen best in FIG. 7 the elongate sleeve 78 includes a plurality of longitudinally aligned, arcuate annular recesses 100 therein. A plurality of position-locking members, in the form of ball bearings 102 are adapted to seat within recesses of the sleeve, and also to engage within openings (to be described later) in the wall of the upper frame section 22 to positively retain the sleeve 78 in a fixed longitudinal position relative to said section. In order to permit adjustment of the sleeve 78 relative to the upper support section 22 the ball bearings 102 are permitted to withdraw from the annular recesses 100 in a manner to be described in detail hereinafter.

Figures 5, 6, 8, 9:
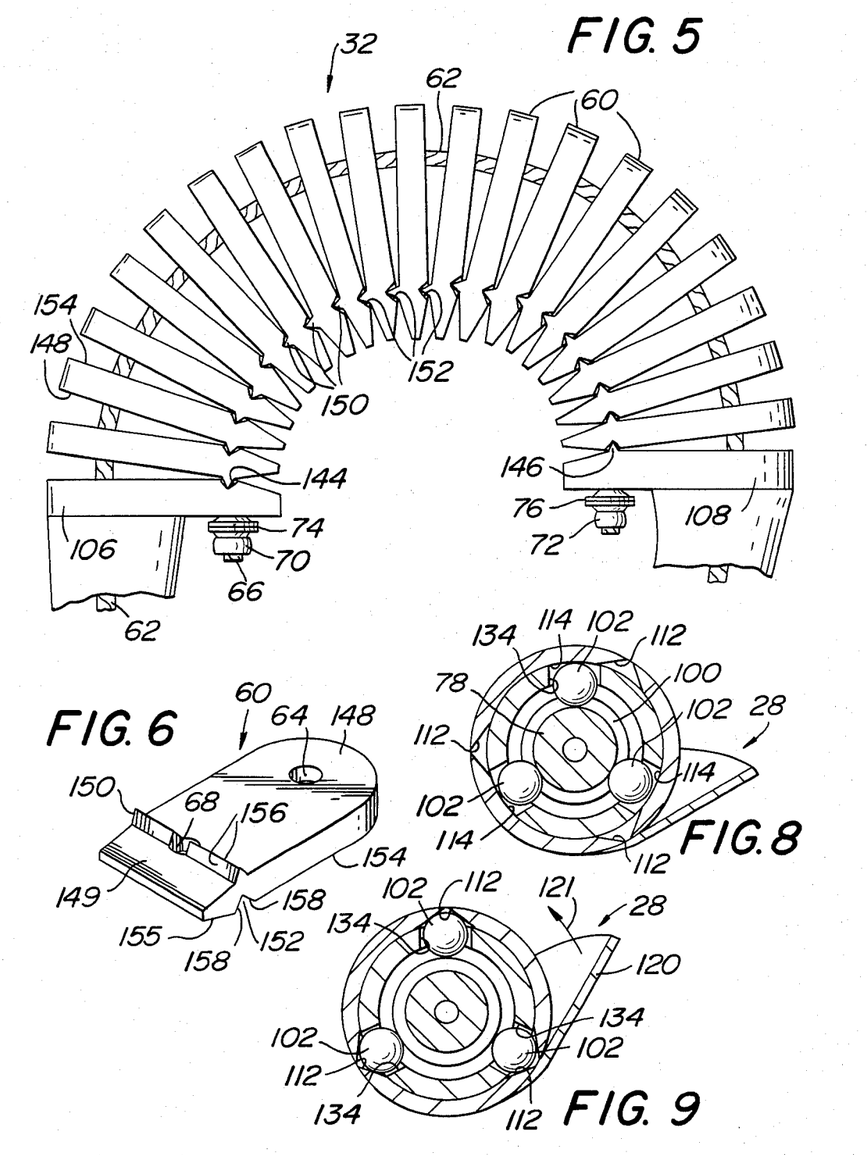
FIG. 5 is an enlarged fragmentary side elevational view illustrating a flexure assembly of the system with elements thereof positioned to illustrate a bending condition.
FIG. 6 is an enlarged perspective view of a slug employed in the flexure assemblies of the system.
FIG. 8 is an enlarged sectional view taken along line 8—8 of FIG. 7.
FIG. 9 is an enlarged sectional view similar to FIG. 8, but showing the elements oriented in a different position.

Referring specifically to FIG. 8 it should be noted that three, position-locking ball bearings 102 are located about the periphery of one of the annular recesses 100. A similar set of three ball bearings is positioned in an annular recess located below the recess shown in FIG. 8. Only one ball bearing of each set is illustrated in FIG. 7. Although six ball bearings are utilized in the preferred embodiment of the invention, the specific number and location of these ball bearings can be varied.

Referring to FIG. 7 the compression spring 80 is positioned between the base of the elongate sleeve 78 and the upper surface of an upper support pad 106 of the flexure assembly 30. This compression spring imparts an upward force to the sleeve 78, as viewed in FIG. 7. This upward force causes the ball bearings 102 to move out of their respective recesses when said ball bearings are free to move in a radially outward direction, thereby permitting the sleeve 78 to move upwardly. Upward movement of the sleeve 78 maintains the cable 62 connected thereto in a taut condition.

Referring specifically to FIGS. 8-10 the actuating mechanism 28 will now be described. This mechanism operates to permit the ball bearings 102 to move radially outwardly from their respective annular recesses 100 to thereby permit adjustment of the predetermined angular range through which the flexure assemblies 30 and 32 can freely move. The adjustment mechanism 28 includes a collar 110 rotatably secured about the outer periphery of the frame section 22 (FIG. 7). A plurality of tapered recesses 112 are machined into the inside periphery of the collar, and are spaced-apart to align with the three annularly spaced-apart ball bearings 102 in each set of said ball bearings.

FIG. 8 shows the collar 110 in the position it normally assumes, with the recesses 112 therein being out of radial alignment with the ball bearings 102. In this position inner surface regions 114 of the collar between the spaced-apart recesses 112 provide obstructing surfaces to prevent the ball bearings from moving radially out of the annular recesses 100 of the elongate sleeve 78.

Thus, in the normal position of the collar 110 the sleeve 78 is maintained in a fixed position within the upper frame section 22 due to the connection between the sleeve and frame section provided by the ball bearings.

Referring to FIG. 10 a torsion spring 116 has one of its free ends positioned within a slot 118 located in a tab, or button 120 of the collar 110. This tab is engaged by the skier for the purpose of rotating the collar in the direction indicated by arrow 121 in FIG. 9. The opposite end of the torsion spring is engaged within a slot 122 of an upper retaining cap 124 which preferably is welded to the outer periphery of the frame section 22. This torsion spring 116 normally biases the collar 110 into the position illustrated in FIG. 8 to thereby retain the ball bearings 102 in their respective annular recesses 100. The position of the collar indicated in FIG. 8 is maintained by the cooperation between a downwardly projecting ledge 126 of the collar and an upwardly projecting ledge 128 of a lower retaining cap 130. This later retaining cap, like the retaining cap 124, preferably is welded to the outer periphery of the frame section 22.

Referring specifically to FIG. 9 the actuating tab 120 is pressed in the direction indicated by the arrow 121 to rotate the collar 110 against the counteracting force of the torsion spring 116 to align the recesses 112 with respective ball bearings 102. In this position the ball bearings are free to move radially out of their associated annular recesses 100, and actually will be forced out of these recesses by the upward linear movement of the sleeve 78 caused by the compression spring 80. Rotation of the collar 110 in the direction of arrow 121 is limited by the cooperation of a downwardly projecting ledge 127 of the collar with an upwardly projecting ledge 129 of the lower retaining cap 130.

It should be noted that with the collar 110 in the orientation illustrated in FIG. 9 the compression spring 80 acts to drive the sleeve 78 to its uppermost setting, i.e., the lower set of ball bearings 102 is in the lowermost groove 100. With the collar 110 being manually maintained in the sleeve release position illustrated in FIG. 9 the skier can then bend his or her knee to a predetermined angle, representing the angle the skier desires to assume when skiing. As the skier bends at the knees the sleeve 78 will be forced downwardly against the opposing force of the compression spring 80 to permit the slugs 60 to pivot with respect to each other while still maintaining the cable 62 taut. When the skier reaches a desired position the tab 120 is released to cause the collar 110 to be rotated by torsion spring 116 back to the position illustrated in FIG. 8, thereby forcing the ball bearings 102 into aligned annular recesses 100 of the sleeve. This sets the angle through which the knees can freely bend without encountering substantial resistance.

It should be noted that the various ball bearings 102 extend into aligned passages 134 in the wall of the upper frame section 22. The ball bearings 102 are prevented from falling out of the support section 22 by the collar 110 which closes the passages. The collar 110 can include one or more enlarged openings (not shown) which can be aligned with the openings 134 in the upper frame section 22 for the purpose of initially inserting the ball bearings 102 into the interior of said rod. After the ball bearings have been inserted into the frame section 22 the collar 110 is located and maintained in a position to prevent the openings in it, through which the ball bearings initially were loaded, from becoming aligned with the spaced-apart passages 134 through the frame section 22. This prevents the individual ball bearings 102 from falling out of the upper frame section 22.

In the preferred embodiment of this invention the constructional arrangement of the flexure assemblies 30 and 32 are identical. Referring specifically to FIG. 3 the upper support pad 106 is welded to the lower end of the upper support frame section 24 to provide an interface with the slugs 60 and also to support one end of the compression spring 80. A similar lower support pad 108 is welded to the upper end of one of the legs of the U-shaped lower bridging section 34 to likewise provide an interface with the slugs 60. As can be seen best in FIG. 5 the surface of the upper support pad 106 engaging an adjacent slug 60 includes a recess 144 formed in it, and the surface of the lower support pad 108 engaging the lowermost slug 60 includes a ridge 146 in it. The recess 144 is identical to the recessess provided in each of the slugs 60, and the ridge 146 is identical to the ridges provided in each of said slugs 60. The exact construction of these recesses and ridges will be described in detail hereinafter.

Referring specifically to FIG. 6, the detailed construction of one of the slugs 60 is illustrated. This slug includes an elongate passageway 64 adjacent the forward end thereof (the end closest to the skier's knee) and a centrally located passageway 68 located adjacent the rear end thereof. As explained earlier the passageway 64 in each slug aligns with similar passageways 64 through the other slugs in the stack and the power cable 62 is received through these aligned passageways. Likewise the passageway 68 in each slug aligns with similar passageways 68 through the other slugs in the stack, and the adjustment cable 66 is received through these aligned passageways.

Still referring to FIG. 6 the upper surface 148 of each slug includes a laterally extending ridge 150 which is interrupted in the middle thereof by the passageway 68. A laterally extending recessess 152 is provided in the bottom surface 154 of the slug in vertical alignment with the laterally extending ridge 150 on the adjacent upper surface 148.

As can be seen in FIGS. 3 and 7, segments 149 and 155 of the upper and lower surfaces 148 and 154, respectively, are located rearwardly of the vertically aligned ridge 150 and recess 152 of each slug and are inclined to cooperate with corresponding inclined segments of adjacent slugs to define a back taper angle between the adjacent slugs 60 of the flexure assemblies 30 and 32. This back-taper angle permits rotational movement of the slugs 60 relative to each other about the fulcrum established by the engagement of the laterally extending ridges 150 of said slugs with the recesses 152 of adjacent slugs, as is illustrated best in FIG. 5.

An extremely important feature of this invention resides in the fact that the interaction of the laterally extending ridges 150 with adjacent laterally extending recesses 152 limit, and in fact virtually preclude rotational twisting of the slugs relative to each other. This prevents failure of the flexure assemblies 30 and 32, and also helps to absorb and reduce twisting loads generally imposed upon the human knee joints, particularly when a skier falls. It should be pointed out that the taut adjustment cable 66 provides a beneficial function in maintaining the apex of each ridge 150 seated against the base of its cooperating recess 152 to assist in preventing the rotational twisting movement between the adjacent slugs 60 of the flexure assemblies.

In order to prevent undesired wear of the inclined surfaces 156 of the ridges 150 and the inclined surfaces 158 of the recesses 152 it is desirable to design the slugs so that they can move relative to each other through their full angular range, without the inclined surfaces 156 and 158 rubbing excessively against each other. To accomplish this result it is preferred that the recess angle (the included angle between the inclined surfaces 158 of the recess) equal the sum of the ridge angle (the included angle between inclined surfaces 156 of the ridge) and the back taper angle (the included angle between adjacent inclined rear segments 149 and 155 of the top and bottom surfaces of adjacent slugs). The recess angle preferably should be no less than the sum of the ridge angle and the back taper angle, and preferably should be not more than 10% greater than said sum.

In operation the back taper angle determines the maximum angular movement that can be achieved, or established between the adjacent slugs 60. In view of the fact that the recess angle is at least as great as the sum of the back taper angle and ridge angle, the inclined surfaces of the ridge will not engage the inclined surfaces of the recesses throughout the full range of angular movement permitted by the back taper angle. Accordingly, very little wear occurs at the fulcrum established between adjacent slugs. The provision of the taut alignment cable 66 provides for a uniform flexure of the flexure assemblies 30 and 32 by maintaining the ridges 150 in proper seated position within cooperating recesses 152.

As described thus far the quick-acting adjustment system 26 permits the setting of a basic support point for the flexure assemblies 30 and 32 to permit said assemblies to freely move through a predetermined angle. In other words the flexure assemblies are free to move through the desired angular position up to the support point without any substantial resistance to flexure. Thereafter, the power cable becomes taut and acts through a dampening spring set 82 to assist in absorbing excessive energy imposed on the brace 12 by the skier.

The dampening spring set 82 is designed to provide a varing resistance to flexure of the flexure assemblies 30 and 32 beyond the set point, to thereby absorb excessive energy imposed on the brace 12 by the human body as the skier is moving over rough terrain. In particular, the spring set permits the brace 12 to absorb the bumps by permitting the skier's legs to continually bend beyond the set point against a dampening resistive force imposed by said spring set.

The brace 12 also employs a hydraulic system, to be described hereinafter, to dampen the spring rate of the spring set 82 in a direction tending to urge the skier back to the set point, after flexure beyond said set point has occurred. In other words the brace 12 basically includes a fluid actuated shock absorbing system so that the spring rate of the spring set 82 is controlled, or dampened to permit the skier to come back easily to the support point, thereby eliminating the bounciness that otherwise might exist.

Referring to FIG. 3 the interior surface of the upper frame section 24 is internally threaded for receiving a threaded plug 200 therein. The shaft 86 passes through an opening in the base of plug 200, and then through an oil seal 204 positioned adjacent the base of said plug. This oil seal which can be a conventional spring loaded Teflon seal, such as is sold by Bal Seal Engineering Company, 620 W. Warner Avenue, Santa Anne, Calif. 92707, seals against the inner periphery of the support rod 24 to provide an upper seal for a chamber 206 in which hydraulic fluid, e.g., oil, is retained. The base of the hydraulic fluid chamber 206 is provided by a lower oil seal 220 which can be a spring loaded seal indentical to the upper seal 204. The seal 220 sits on top of a substantially flat plate 222 welded to the inner periphery of the frame section 24. Thus, the lower oil seal 220, in conjunction with the upper oil seal 204 and the inner periphery of the upper frame section 24 define the chamber 206 in which hydraulic oil is retained.

Figure 4:
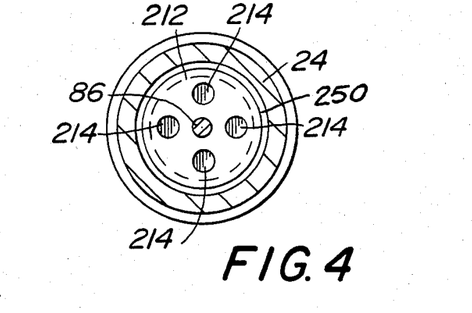
FIG. 4 is an enlarged sectional view taken along line 4—4 of FIG. 3.

Referring to FIGS. 3 and 4, the upper end of the shaft 86 is provided with a slot 208 for receiving the working end of a screwdriver (not shown) to permit the lower threaded end 210 of the shaft to be secured within the upper threaded section of the connector 84. A piston 212 is secured to the shaft 86 and includes a plurality of passages 214 extending through it, four such passages being provided in the illustrated embodiment. A check valve 216, basically in the form of a thin metal washer, is located above the piston 212 and is adapted to close off the passages 214 to the movement of hydraulic fluid from above the piston 212 to a position below said piston.

Referring specifically to FIG. 3 the dampening spring set 82 is stacked in a column approximately six inches high. This set and includes approximately 160 disk-type springs 224, such as Belleville springs adapted to deflect under a predetermined load. Belleville springs utilizable in this invention are sold by Rolex Company, 385 Hillside Avenue, Hillside, N.J. 07275.

In the illustrated embodiment the spring set 82 is divided into three discrete sections 230, 232 and 234, to provide progressively greater resistance to bending. Each section is approximately 2 inches in height. In the first set 230 nested pairs of springs (i.e., two springs in parallel) are stacked in series and each pair has a maximum deflection rated at 300 pounds (660 kilograms). The middle section 232 includes nested triples (i.e., three springs in parallel) rated at 450 pounds (990 kilograms) and being stacked in series. The third section 234 includes nested quads (i.e., four springs in parallel) having a maximum deflection rated at 600 pounds (1320 kilograms) and being stacked in series.

An analysis of dynamic loading indicates that a maximum sitz load of 250 to 500 pounds generally is imposed upon the spring set 82, depending upon the weight of the skier and the angle of knee bend determined by the set point of the flexure assemblies 30 and 32. Thus, the spring set may be partially depressed to support this load.

When a skier hits a bump, such as when skiing on rough terrain, a maximum dynamic load of as much as 5 G's (1250–2500 pounds) can be imposed upon the brace 12. Under these conditions the springs will gradually collapse, or deflect to thereby absorb this dynamic loading. Specifically, the deflection of the spring set allows for additional knee bending beyond the predetermined set point, to thereby permit the gradual dissipation of the shock which otherwise would be abruptly absorbed by the skier's body.

In the preferred system of this invention the six inch spring set 82 is designed to deflect a maximum of approximately one inch, thereby providing for one inch of movement of the power cable 62. This equates to approximately 40° of angular movement of the flexure assemblies 30 and 32 to thereby permit a corresponding additional angular movement of the knees of the skier beyond the set point. This additional dampened movement, for the purpose of absorbing energy imposed upon the body weight support system 10, is not possible with the body weight support system described in copending application Ser. No. 411,404, which already has been incorporated herein by reference.

It should be noted that unimpeded, or unrestricted downward movement of the power cable 62 is permitted by the provision of the passages 214 through the piston 212 as the springs 224 deflect. Specifically, during this downward movement the check valve 216 is open to permit the substantial unimpeded flow of hydraulic fluid through these passages. This prevents the high viscosity of the fluid from excessively impeding, or retarding the downward movement of the power cable 62 as the individual disk springs 224 deflect under dynamic loading.

However, upward movement of the power cable 64 to reposition the flexure assemblies 30 and 32 back to the desired set point is retarded, or dampened by the inclusion of the check valve 216 which precludes hydraulic fluid from passing through the passages 214. With these passages closed the hydraulic fluid only is permitted to move slowly through a small restrictive annular passage 250 established between the side peripheral edge of the piston 212 and the inner periphery of the support section 24 (FIG. 4). In a preferred embodiment of this invention the cycle time from the bottom of the stroke (with the individual springs 224 deflected under dynamic loading) to full return to the preset point is approximately one second, and the hydraulic cylinder pressure is in the range of 7,000 pounds per square inch.

The provision of sections in the spring set 82 having different maximum deflection ratings provides for the progressive absorption of energy imparted to the body weight support system 10 under the dynamic conditions encountered by a skier moving over rough terrain. In other words not all of the springs will deflect, or collapse at the same time under dynamic loading conditions, but rather will gradually collapse to gradually absorb the energy. Although a specific arrangement for stacking the springs in three distinct sections has been disclosed, it should be noted that the springs can be nested in various different arrangements to provide the desired load responsive characteristics in the spring set 82.

Referring specifically to FIGS. 1 and 2A the details of ski boot attaching member 38 will be described. Thus, as can be seen member 38 includes a rear arcuate segment 300 adapted to encircle the rear of a ski boot 14 and a pair of front straps 302 and 304 connected to the rear segment 300 and adapted to be secured about the front of the boot. The securing mechanism can be of any desired construction, and is illustrated herein as including a conventional link 306 attached to the end of the strap 302. The link is selectively positionable within a desired groove 308 or 310 of a clasp 312 pivotably secured to the opposed strap 304.

As can be seen best in FIG. 2A a mounting plate 314 is secured by suitable fastners (not shown) to the rear arcuate segment 300 of the boot attaching member. A pair rearwardly projecting ears 316 and 318 are employed to pivotably secure the rear arcuate segment 300 to a forward section 320 of a connecting link 322 through a laterally disposed pivot pin 324. A rear section 326 of the connecting link 322 includes a central passage 328 for adjustably receiving the vertical support rod 36 of the brace 12. When the attaching member 38 is in its desired positioned on the vertical support rod 36 a screw 330, or other suitable tightening means, is employed to tighten the connecting link 322 on said support rod.

In the preferred embodiment of this invention the forward section 320 of the connecting link 322 is rotatably joined to the rear section 326 through an elongate axle 332 to permit rotational movement of the rear section 326 relative to the ski boot attaching member 38 so that virtually the entire brace 12 can be laid on its side as said shoe attaching member 38 is being secured to the skier's boot. This definitely facilitates the attaching operation.

The pivot connection provided by the laterally disposed pivot pin 324 permits the skier to move forwardly and backwardly relative to his ski boots to assume a desired attack position. Moreover, if the skier leans backward to a position in which his or her buttocks is not positioned over the ski boots little or no support will be provided by the brace 12. When this occurs the skier will know that he or she is in a poor skiing posture, thereby prompting the skier to change his or her body position. Thus, the provision of the pivot axis established by the pivot pin 324 facilitates use of the body weight supporting system 10 of this invention as a teaching and/or training aid for skiers.

It should be noted that the swivel movement permitted between the forward section 320 and rear section 326 of the connecting link 322 permits lateral movement of the skier's body during a ski run, while the unique arrangement of the flexure assemblies 30 and 32 acts to preclude excessive lateral movement of the skier's knee relative to the rest of his leg, and also undesired twisting of the knee. Thus, lateral mobility of the skier's body is permitted while at the same time undesired lateral, or twisting movement of the knee is precluded.

As in the earlier referenced Waddell application (Ser. No. 411,404) the ski braces described heretofore can be incorporated into a garment, such as a pair of ski pants. The manner of securing the ski braces of this invention into the garment will be virtually the same as described in the Waddell application, the subject matter of which already has been incorporated by reference into the instant application.

Briefly summarizing this aspect of the invention each leg of the garment includes a pair of longitudinally extending passageways formed by sewing respective fabric strips onto the inside of each leg. Each of these passageways is arranged to receive therein a respective upper frame section (i.e., 22, 24) flexure assembly (i.e., 30, 32) and spaced-apart upper portions of the legs forming the U-shaped bridging section 34. The legs of the U-shaped bridging section 34 extend through respective openings in each of the passageways, which can be openings provided in the fabric strips, so that the lower portion of the brace is exposed within the interior of the pant's leg for ready connection to the ski boot.

The tab 120 of the adjustment means can be positioned to extend through an opening in the outer layer of the garment to permit easy access for adjusting the angle through which the flexure assemblies 30 and 32 are free to bend without encountering significant resistance.

As will thus be appreciated from the foregoing, the support system of the instant invention has a wide variety of applications other than the specifically disclosed skiing application. For example, the system can be used whenever it is desirable to provide support for a person who must stand with the knees bent in a predetermined position for an extended period of time. One example of such applications is use by farm workers for manual picking of low growing crops, inasmuch as the system can provide capability for total support of the body while allowing the wearer to move in a normal manner.

Insofar as the advantages of the system to skiers are concerned, the adjustment of the degree of flexure of the angle enables skiers to readily set the point at which the knee bend angle produces total support for the body, thereby resulting in virtually weightless skiing based on personal preference. The total support provided by the system not only relieves leg strain but also tends to center the skier's weight over the skis which is desirable for effective skiing. The energy dampening system of this invention provides a damped supportive force which does not oscillate or rebound, thereby insuring that the skier can maintain effective control, while at the same time absorbing shocks imposed on the skier's body.

The top-fitting plastic thigh support member 20 spreads the body weight over a large surface on the rear side of the upper leg so that there are no pressure points which would tend to be uncomfortable. Moreover, by virtue of the securement of the system to the boots, most of the body weight is transferred to the boots. Thus, the skier can "sit" on the system while remaining in a good attack posture. The resulting relaxation of the leg muscles during such operation eliminates the normal muscle strain and fatigue associated with skiing, thereby making skiing a much more pleasurable recreation.

The unique arrangement and construction of the slugs 60 employed in the flexure assemblies will prevent the imposition of undesired torsional stresses on the skier's leg, while at the same time permitting normal bending of the skier's knee.

The location of the laterally spaced-apart support means halfway between the rear and side of the leg puts the support means out of the way during a fall, since during most falls the skier either lands on the rear portion of the legs or on the side-hip area.

Owing to the height adjustment means for establishing the connection to the boot the system can be utilized by skiers of various heights. The adjustment feature of the support system of the instant invention enables one to accurately reset the system to any desired position, thereby compensating for any wear-induced changes which may occur over the long life of the system.

The movable connections between the member attached to the boot and the upwardly directed supports secured to the wearer's leg permits significantly more latitude in body movement of the skier than heretofore has been achievable. Moreover, this connection makes the instant invention quite suitable for use in teaching and/or training applications by encouraging the skier to maintain a proper skiing posture in order to obtain the body-supporting benefits of the invention.

By virtue of the foregoing features of the instant invention persons heretofore unable to ski due to some physical defect, such as amputees, persons with muscle or nerve disorders, bad knees, etc., can ski effectively and safely. Thus, the instant invention provides for safer, more aggressive and effective skiing for all persons.

Without further elaboration the foregoing will so fully illustrate my invention, that others may, by applying current or future knowledge, adopt the same for use under various conditions of service.

I claim:

1. A body weight support system for releasable securement to at least one leg of a person, comprising upper support means, lower support means and flexure means, said upper support means extending along the thigh and terminating at its upper end adjacent the buttocks-high interface to form a seat and terminating at its lower end adjacent the knee, said lower support means extending along the calf and terminating at its upper end adjacent the knee and at its lower end adjacent the foot, said flexure means being located adjacent said knee and being connected between said upper and lower support means, said flexure means being adjustable for permitting the person to repeatedly freely bend and unbend said knee through any angular range up to a predetermined angle of bend at which a resistance exists to further flexure, said upper and lower support means including securement means for releasably securing said system to said leg, characterized by tensioning means for setting said predetermined angle of bend and energy dampening means separate from said tensioning means for establishing a resistance to movement of said flexure means beyond said predetermined angle and for permitting dampened flexure beyond said predetermined angle to absorb shocks transmitted to the body of the wearer.

2. The body weight support system of claim 1, characterized in that said energy dampening means includes spring means for deflecting under loading exceeding a predetermined level.

3. The body weight support system of claim 2, characterized in that the spring means includes a set of spring elements stacked in a column.

4. The body weight support system of claim 3, characterized in that the set of spring elements includes sections with different maximum deflection ratings for permitting gradual dampened movement of the flexure means beyond said predetermined angle.

5. The body weight support system of claim 4, characterized in that the sections of the set of spring elements having differing maximum deflection ratings include differing numbers of discs nested in parallel.

6. The body weight support system of claim 1, characterized by additional dampening means for assisting in controlling the rate of movement of the energy dampening means in a direction returning the flexure means to said predetermined angle.

7. The body weight support system of claim 6, characterized in that said additional dampening means is a fluid-actuated dampening system.

8. The body weight support system of claim 3, characterized by additional dampening means for assisting in controlling the rate of movement of the energy dampening means in a direction returning the flexure means to said predetermined angle.

9. The body weight support system of claim 8, characterized in that said additional dampening means is a fluid-actuated dampening system.

10. The body weight support system of claim 1, characterized in that said flexure means is adjustable for establishing different angular ranges of flexure through which said knee can be freely bent.

11. The body weight support system of claim 10, characterized in that said flexure means comprises plural elements coupled to one another through said tensioning means whereupon said elements can pivot with respect to one another with the degree of pivoting being established by said tensioning means.

12. The body weight support system of claim 11, characterized in that said tensioning means includes an elongate, flexible cable passing through said plural elements and adjustment means for controlling the degree of tension on said cable.

13. The body weight support system of claim 12, characterized in that said energy dampening means includes a set of spring elements stacked in a column, said flexible cable extending through aligned passages in said set of spring elements.

14. The body weight support system of claim 13, characterized by connecting means joining said cable to an additional dampening means for assisting in controlling the rate of movement of the stack of discs in a direction opposed to the direction of movement of the stack during dampened flexure of the flexure means.

15. The body weight support system of claim 14, characterized in that said additional dampening means includes an elongate rod secured to the connecting means and extending through a chamber in which hydraulic fluid is retained, and a piston secured to said rod within said chamber for cooperating with the hydraulic fluid to dampen the movement of the stack of springs in a direction opposed to the direction of movement of the stack during dampened flexure of the flexure means.

16. The body weight support system of claim 15, characterized by the provision of passages through said piston and a movable valve means overlying said passages for permitting hydraulic fluid to pass through said passages as the spring elements are being deflected to provide dampened flexure of the flexure means and for preventing hydraulic fluid from passing through said passages during movement of said spring elements in a direction opposed to the deflecting direction of movement of said spring elements to thereby dampen the return movement of the set of spring elements from a deflected state.

17. The body weight support system of claim 11, wherein said elements are substantially flat members stacked upon each other and including cooperating fulcrum means between adjacent members about which said members can pivot with respect to one another.

18. The body weight support system of claim 17, characterized in that the fulcrum means includes a ridge of one member engaging within a cooperating recess of an adjacent member, said ridge and recess associated with adjacent members extending generally transverse to the plane of flexure of said members.

19. The body weight support system of claim 17, characterized in that each of the elements includes a forward end adapted to be located adjacent the knee and a rearward end adapted to be located remote from said knee, confronting surface regions of adjacent elements located rearwardly of the fulcrum means being inclined away from each other to provide a back taper angle for permitting pivotable movement of said elements about said fulcrum means.

20. The body weight support system of claim 19, characterized in that the fulcrum means includes a ridge of one member engaged within a cooperating recess of an adjacent member, said ridge and recess associated with adjacent members extending generally transverse to the plane of flexure of said members.

21. The body weight support system of claim 20, characterized in that one surface of each element includes an elongate ridge and the opposed surface includes an elongate recess, the ridge and recess of each element being vertically aligned with each other and being interrupted by a passageway extending through said element, said passageways of adjacent elements being aligned for receiving a tensioning means to maintain the transversely extending, confronting ridge and recess of adjacent elements in engagement with each other as said elements are pivoted with respdct to one another.

22. The body weight support system of claim 20, characterized in that the transversely extending recesses include inclined surfaces and said transversely extending ridge include inclined surfaces, the angle defined by the inclined surfaces of the recesses being no less than the sum of the back taper angle between adjacent elements and the included angle between the inclined surfaces of the ridges.

23. The body weight support system of claim 22, characterized in that one surface of each element includes an elongate ridge and the opposed surface includes an elongate recess, the ridge and recess of each element being vertically aligned with each other and being interrupted by a passageway extending through said element, said passageways of adjacent elements being aligned for receiving a tensioning means to maintain the transversely extending, confronting ridge and recess of adjacent elements in engagement with each other as said elements are pivoted with respect to one another.

24. The body weight support system of claim 12, characterized in that one adjustment means is attached to one end of said flexible cable for establishing the degree of tension in said cable.

25. The body weight support system of claim 24 characterized in that said upper support means incudes a hollow support rod, said adjustment means including an elongate sleeve movably mounted within said support rod, said sleeve including a plurality of annular recesses disposed along the elongate dimension thereof, a plurality of recess-engaging members maintained in a fixed position within said hollow support rod for engaging within selected annular recesses to maintain said sleeve in a desired position relative to said rod, and means for permitting release of said recess-engaging members from the annular recesses to permit movement of the elongate sleeve within said rod to thereby adjust the tension in the cable.

26. The body weight support system of claim 25 characterized in that the recess-engaging members are generally spherical ball bearings engaged within openings in the hollow support rod, said means for permitting release of said ball bearings includng a collar rotatable about the outer periphery of the support rod and including recessed regions adapted to align with the openings in the support rod in which the ball bearings are retained for receiving said ball bearings as they move out of engagement with an aligned annular recess of the elongate sleeve.

27. The body weight support system of claim 24 characterized by connecting means for joining the opposed end of said flexible cable to additional dampening means for controlling movement of the energy dampening means in a direction opposed to the direction of movement of said energy dampening means during dampening flexure of the flexure means beyond said predetermined angle.

28. A support system for releasable securement to at least one leg of a person and including flexure means located adjacent the knee, said flexure means including including a plurality of substantially flat elements stacked upon each other, said elements including cooperating fulcrum means between adjacent elements about which said elements can pivot with respect to one another, each of said elements including a forward end adapted to be located adjacent the knee and a rearward end adapted to be located remote from said knee, confronting surface regions of adjacent elements located rearwardly of the fulcrum means being inclined away from each other to provide a back taper angle for permitting pivotable movement of said elements about said fulcrum means.

29. The support system of claim 28 characterized in that the fulcrum means includes a ridge of one element engaged within a cooperating recess of an adjacent element, said ridge and recess associated with adjacent elements extending generally transverse to the plane of flexure of said elements.

30. The support system of claim 29 characterized in that one surface of each element includes an elongate ridge and the opposed surface includes an elongate recess, the ridge and recess of each element being vertically aligned with each other and being interrupted by a passageway extending through said elements, said passageways of adjacent elements being aligned for receiving tensioning means adapted to maintain transversely extending, confronting ridges and recesses of adjacent elements in engagement with each other as said elements are pivoted with respect to one another.

31. The support system of claim 29 characterized in that the transversely extending recesses include inclined surfaces and said transversely extending ridges include inclined surfaces, the angle defined by the inclined surfaces of the recesses being no less than the sum of the back taper angle between adjacent elements and the included angle between the inclined surfaces of the ridges.

32. The support system of claim 31 characterized in that one surface of each element includes an elongate ridge and the opposed surface includes an elongate recess, the ridge and recess of each element being vertically aligned with each other and being interrupted by a passageway extending through said element, said passageways of adjacent elements being aligned for receiving tensioning means adapted to maintain transversely extending, confronting ridges and recesses of adjacent elements in engagement with each other as said elements are pivoted with respect to one another.

33. The support system of claim 30 characterized in that each element includes an additional passageway through it in a region forwardly of the ridge and recess, said additional passageways of adjacent elements being aligned for receiving an elongate flexible cable through them.

34. The support system of claim 32 characterized in that each element includes an additional passageway through it in a region forwardly of the ridge and recess, said additional passageways of adjacent elements being aligned for receiving an elongate flexible cable through them.

35. A body weight support system for releasable securement to at least one leg of a person, comprising upper support means, lower support means and flexure means, said upper support means extending along the thigh and terminating at its upper end adjacent the buttocks-thigh interface to form a seat and terminating at its lower end adjacent the knee, said lower support means extending along the calf and terminating at its upper end adjacent the knee and at its lower end adjacent the foot, said flexure means being located adjacent said knee and connected between said upper and lower support means to enable the person to freely bend said knee through an angular range up to a predetermined angle at which a resistance exists to further flexure, said upper and lower support means including securement means for releasably securing said system to said leg, characterized by energy dampening means for establishing a resistance to movement of said flexure means beyond said predetermined angle and for permitting dampened flexure beyond said predetermined angle to absorb shocks transmitted to the body of the wearer, said energy dampening means including a set of spring elements stacked in a column, said set including sections with different maximum deflection gradings for permitting gradual dampened movement of the flexure means beyond said predetermined angle.

36. The body weight support system of claim 35, characterized in that the section of the set of spring elements having different maximum deflection ratings include differing numbers of discs nested in parallel.

37. A body weight support system for releasable securement to at least one leg of a person, comprising upper support means, lower support means and flexure means, said upper support means extending along the thigh and terminating at its upper end adjacent the buttocks-thigh interface to form a seat and terminating at its lower end adjacent the knee, said lower support means extending along the calf and terminating at its upper end adjacent the knee and at its lower end adjacent the foot, said flexure means being located adjacent said knee and connected between said upper and lower support means to enable the person to freely bend said knee through an angular range up to a predetermined angle at which a resistance exists to further flexure, said upper and lower support means including securement means for releasably securing said system to said leg, characterized by energy dampening means for establishing a resistance to movement of said flexure means beyond said predetermined angle for permitting dampened flexure beyond said predetermined angle to absorb shocks treansmitted to the body of the wear, said flexure means comprising plural elements coupled to one another through a tensioning means, said tensioning means including an elongate, flexible cable passing through said plural elements and means attached to one end of said flexible cable for setting tension in said cable, connecting means for joining the opposed end of said flexible cable to additional dampening means for controlling movement of the energy dampening means in a direction opposed to the direction of movement of said energy dampening means during dampening flexure of the flexure means beyond said predetermined angle.

38. A body weight support system for releasable securement to at least one leg of a person, said support system including a flexure means located adjacent a knee of said person and being connected between upper and lower support means that are attachable to the leg of said person, said flexure means enabling the person to repeatedly freely bend and unbend said knee through any angular range up to a predetermined angle of bend at which a resistance exists to further flexure, tensioning means for setting said predetermined angle of bend, and energy dampening means separate from said tensioning means for establishing a resistance to said flexure means beyond said predetermined angle and for permitting dampened flexure beyond said predetermined angle to absorb shocks transmitted to the body of the wearer.

39. The body weight support system of claim 38, characterized in that said energy dampening means includes spring means for deflecting under loading exceeding a predetermined level.

40. The body weight support system of claim 39, characterized in that the spring means includes a set of spring elements stacked in a column.

41. The body weight support system of claim 38, characterized by additional dampening means for assisting in controlling the rate of movement of the energy dampening means in a direction returning the flexure means to said predetermined angle.

42. The body weight support system of claim 41, characterized in that said additional dampening means is a fluid-actuated dampening system.

43. The body weight support system of claim 40, characterized by additional dampening means for assisting in controlling the rate of movement of the energy dampening means in a direction returning the flexure means to said predetermined angle.

44. The body weight support system of claim 43, characterized in that said additional dampening nmeans is a fluid-actuated dampening system.

45. The support system of claim 28, characterized in that each element includes a passageway through it in a region forwardly of the fulcrum means, said passageways of adjacent elements being aligned for receiving an elongate flexible cable through them.

* * * * *